(12) United States Patent  (10) Patent No.: US 8,677,514 B1
Jones  (45) Date of Patent: Mar. 25, 2014

(54) FINGER SPLAYING GLOVE

(71) Applicant: Ronald E. Jones, Fort Lauderdale, FL (US)

(72) Inventor: Ronald E. Jones, Fort Lauderdale, FL (US)

( * ) Notice: Subject to any disclaimer, the term of this patent is extended or adjusted under 35 U.S.C. 154(b) by 0 days.

(21) Appl. No.: 13/749,987

(22) Filed: Jan. 25, 2013

(51) Int. Cl.
A41D 19/00 (2006.01)

(52) U.S. Cl.
USPC .................................. 2/161.1; 2/16

(58) Field of Classification Search
USPC .................................. 2/159–164; 602/21, 22
See application file for complete search history.

(56) References Cited

U.S. PATENT DOCUMENTS

| 458,888 | A | * | 9/1891 | Eisele | 441/57 |
|---|---|---|---|---|---|
| 3,231,910 | A |  | 2/1966 | Teglund |  |
| 3,938,207 | A |  | 2/1976 | Drescher |  |
| 4,027,347 | A |  | 6/1977 | Sato |  |
| 4,479,571 | A |  | 10/1984 | Eliot |  |
| 4,602,620 | A | * | 7/1986 | Marx | 602/21 |
| 4,738,447 | A | * | 4/1988 | Brown | 473/450 |
| 4,765,320 | A | * | 8/1988 | Lindemann et al. | 602/22 |
| 5,027,802 | A | * | 7/1991 | Donohue | 602/22 |
| 5,297,541 | A | * | 3/1994 | Hensey | 601/40 |
| 5,538,488 | A | * | 7/1996 | Villepigue | 482/47 |
| 5,636,381 | A | * | 6/1997 | Brogden | 2/161.1 |
| 5,730,658 | A | * | 3/1998 | Kurtz et al. | 473/205 |
| D416,601 | S | * | 11/1999 | Gurley | D21/807 |
| 7,415,735 | B2 | * | 8/2008 | Erickson et al. | 2/163 |
| 7,721,353 | B2 | * | 5/2010 | Saturnio | 2/160 |
| 7,892,194 | B2 | * | 2/2011 | Farrell et al. | 602/21 |
| 8,162,781 | B2 | * | 4/2012 | Heflin, Sr. | 473/448 |
| 8,291,517 | B2 | * | 10/2012 | Taliento et al. | 2/161.1 |

* cited by examiner

Primary Examiner — Richale Quinn

(57) ABSTRACT

A finger splaying glove that includes a plurality of extenders disposed perpendicularly between each of the glove fingers, wherein rotation of a dial disposed dorsally proximal the wrist of the glove slidably engages each of a plurality of cord members whereby each of the plurality of extenders is extended and each of the fingers of a person wearing the glove is splayed apart, whereby symptomology of carpel tunnel syndrome, or other repetitive action or stress related tension or discomfort, is alleviated.

6 Claims, 3 Drawing Sheets

FINGER SPLAYING GLOVE

BACKGROUND OF THE INVENTION

Various types of gloves are known in the prior art. However, what is needed is a finger splaying glove that includes a plurality of extenders disposed perpendicularly between each of the glove fingers wherein rotation of a dial disposed dorsally proximal the wrist of the glove slidably engages each of a plurality of cord members whereby each of the plurality of extenders is extended and each of the fingers of a person wearing the glove is splayed apart whereby symptomology of carpel tunnel syndrome, or other repetitive action or stress related tension or discomfort, is alleviated.

FIELD OF THE INVENTION

The present invention relates to a finger splaying glove, and more particularly, to a finger splaying glove that includes a plurality of extenders disposed perpendicularly between each of the glove fingers wherein rotation of a dial disposed dorsally proximal the wrist of the glove slidably engages each of a plurality of cord members whereby each of the plurality of extenders is extended and each of the fingers of a person wearing the glove is splayed apart whereby symptomology of carpel tunnel syndrome, or other repetitive action or stress related tension or discomfort, is alleviated.

SUMMARY OF THE INVENTION

The general purpose of the finger splaying glove, described subsequently in greater detail, is to provide a finger splaying glove which has many novel features that result in a finger splaying glove which is not anticipated, rendered obvious, suggested, or even implied by prior art, either alone or in combination thereof.

The present finger splaying glove has been devised to enable spaying of the hand of a user wearing the glove. By splaying apart the fingers of the hand wearing the glove, the finger splaying glove is contemplated to alleviate symptoms of carpel tunnel syndrome, tendonitis, and other discomforts caused by repetitive action of the hand.

The present finger splaying glove includes a plurality of extenders disposed perpendicularly between each of the glove fingers at a position proximal to the proximal interphalangeal of each finger of a user wearing said glove. A plurality of cord members are centrally disposed through each of the extenders. Each of the plurality of cord members terminates at a connection point disposed at one end of each respective extender upon the exterior of a respective glove finger.

Each of the plurality of cord members is slidably drawn through a pivot point disposed at an opposite end of each extender relative each connection point. Each of the plurality of cord members is rotationally engaged by means of a dial disposed dorsally upon the glove proximal the wrist, in a position proximally overlying the capitate of a user wearing the glove.

The dial is movable between a plurality of settings. When the dial is moved between each of the plurality of settings, each of the plurality of extenders is extended a specific distance and each of the glove fingers are splayed the specific distance apart. It is contemplated that the specific distance each of the extenders is extenders increases as the dial is rotated from a minimum setting to a maximum setting.

At the minimum setting, the extenders are least extended, and the fingers of a person wearing the glove are least distanced apart. At the maximum setting, the plurality of extenders are extended a maximally extended, and the fingers of a person wearing the glove are most distanced apart.

The finger splaying glove enables splaying of a person's fingers while the muscles in the hand are relaxed, thereby stretching said muscles and alleviating symptomology of carpel tunnel syndrome or other stress related tension in the hand.

Thus has been broadly outlined the more important features of the present finger splaying glove so that the detailed description thereof that follows may be better understood and in order that the present contribution to the art may be better appreciated.

Objects of the present finger splaying glove, along with various novel features that characterize the invention are particularly pointed out in the claims forming a part of this disclosure. For better understanding of the finger splaying glove, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
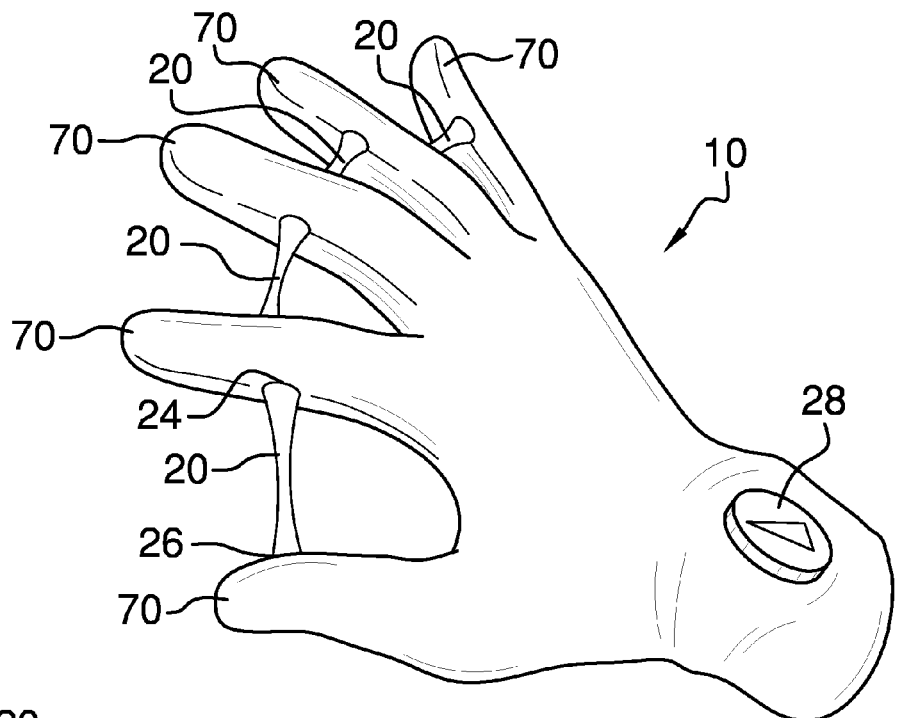
FIG. 1 is an isometric view.
Figure 2:
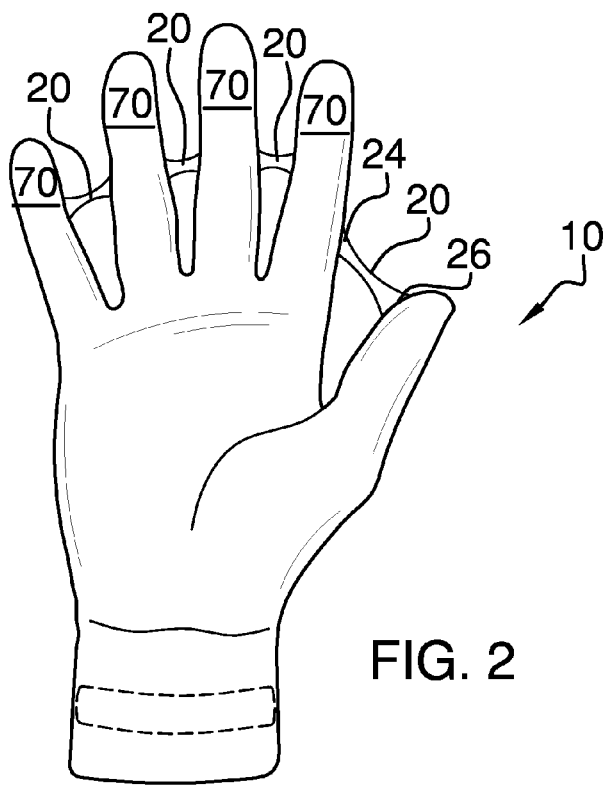
FIG. 2 is a palmer view.
Figure 3:
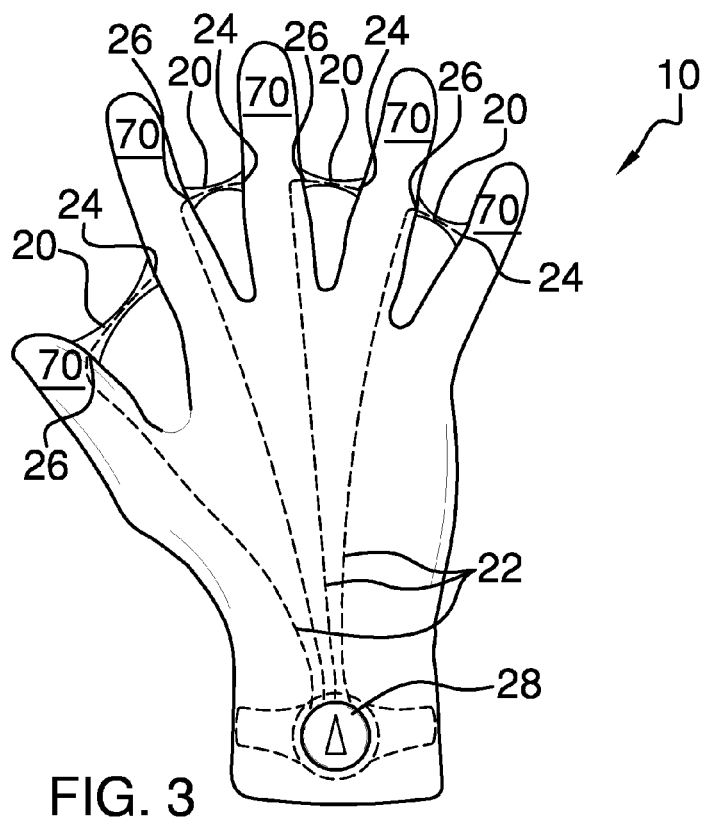
FIG. 3 is a dorsal view with a plurality of extenders extended.
Figure 4:
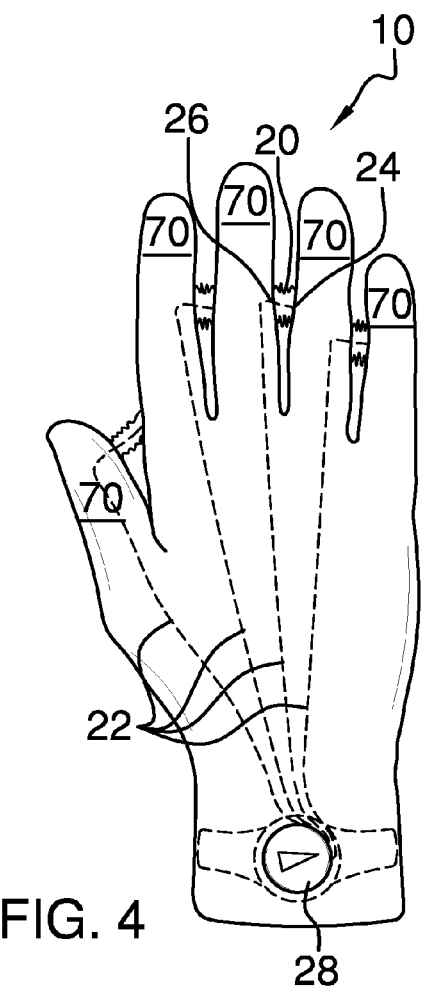
FIG. 4 is a dorsal view with the plurality of extenders compressed.
Figure 5:
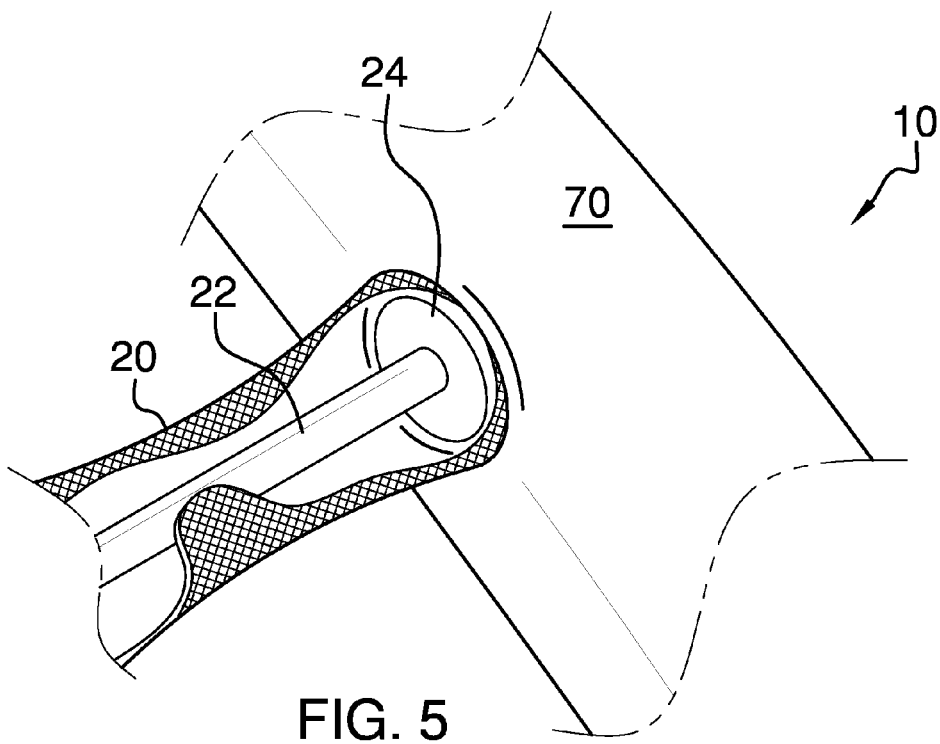
FIG. 5 is a detail view of a connection point.
Figure 6:
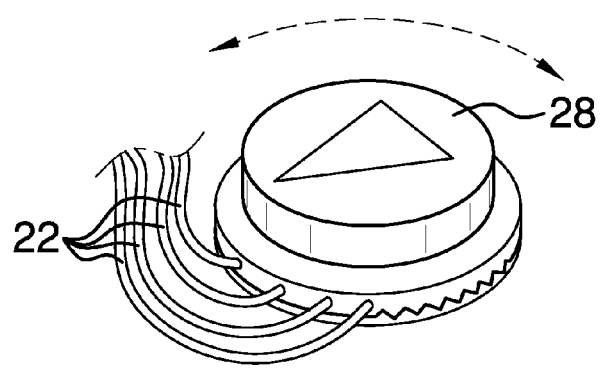
FIG. 6 is a detail view of a dial.

With reference now to the drawings, and in particular FIGS. 1 through 4 thereof, example of the instant finger splaying glove employing the principles and concepts of the present finger splaying glove and generally designated by the reference number 10 will be described.

Referring to FIGS. 1 through 4 a preferred embodiment of the present finger splaying glove 10 is illustrated.

The present finger splaying glove 10 has been devised to assist in the treatment of carpal tunnel syndrome, tendonitis, and other disablements and discomfort of the hand. The present finger splaying glove 10 includes a plurality of extenders 20 disposed perpendicularly between each of the glove fingers 70. Each of the plurality of extenders 20 is positioned between adjacent middle phalanges, proximal to each proximal interphalangeal, of each finger of a wearer wearing the glove 10.

A plurality of cord members 22 is disposed through each of said plurality of extenders 20 and connected to each finger 70 at a respective connection point 24. Each connection point 24 is disposed endwise upon each extender 20. Each cord member 22 is disposed through each extender 20, thence through each of a plurality of pivot points 26 disposed exteriorly upon the glove fingers 70 on the opposite end of each extender 70.

A dial 28 is disposed dorsally proximal the wrist of the glove 10, in a position proximately overlying the capitate of a user wearing said glove 10. The dial 28 is moveable between a plurality of settings. When moved between the plurality of settings, the dial 28 engages each of said plurality of cord members 22 and draws each of said cord members 22 a specific distance through the respective pivot point 26 whereby each of the plurality of extenders 20 is extended to splay the fingers 70 of said glove 10 a predetermined distance apart.

The splaying of the hand of a user wearing the glove 10 may be thusly spayed, and their fingers stretched apart, whereby the symptoms of carpel tunnel syndrome, and other discomforts of the hand, are envisioned to be alleviated.

What is claimed is:

1. A finger splaying glove comprising a glove having a plurality of glove fingers, a plurality of extenders disposed perpendicularly between each of the glove fingers, each of said extenders slidably engaged by each of a plurality of cord members disposed upon the glove, each of said cord members rotationally engaged by means of a dial disposed upon the glove exterior proximal the glove wrist, wherein rotation of the dial pulls each of the plurality of cord members whereby each of the plurality of extenders is extended and each of a finger of a person wearing the glove is splayed apart.

2. The finger splaying glove of claim 1 wherein each of the plurality of cord members is routed through a respective extender and drawn through a pivot point disposed upon the glove exterior of a glove finger endwise upon each extender.

3. The finger splaying glove of claim 2 wherein each cord terminates upon a respective finger of said glove at each of a plurality of connection points, each connection point disposed endwise upon each extender opposite a respective pivot point disposed endwise on the opposite end of said extender.

4. The finger splaying glove of claim 3 wherein the dial is selectively rotatable between a plurality of settings, each of said settings configured to splay the fingers a particular distance apart.

5. The finger splaying glove of claim 4 wherein each of the plurality of extenders is positioned upon the glove to effectuate splaying of a user's hand at the middle phalanges of each finger, each of said extenders positioned proximally adjacent the proximal interphalangeals of respectively adjacent fingers.

6. A finger splaying glove comprising:

a glove having a plurality of glove fingers;

a plurality of extenders disposed perpendicularly between each of the glove fingers at a position proximal respective interphalangeals of a user wearing the glove;

a plurality of cord members centrally drawn longitudinally through each of said plurality of extenders;

a plurality of connection points disposed exteriorly upon the fingers of said glove at one end of each extender, each of said plurality of connection points connecting each of said plurality of cords to each respective finger of said glove;

a plurality of pivot points disposed exteriorly upon the fingers of the glove at an opposite end of each extender relative the connection point, each of said plurality of pivot points slidably housing each of said plurality of cord members;

a dial disposed dorsally proximal the wrist of the glove, said dial rotationally engaging each of said plurality of cord members between a plurality of settings configured to splay the fingers of said glove a predetermined distance apart;

wherein rotation of the dial between the plurality of settings pulls each of the plurality of cord members whereby each of the plurality of extenders is extended and each of a finger of a person wearing the glove are splayed apart.

* * * * *